Figure 2:
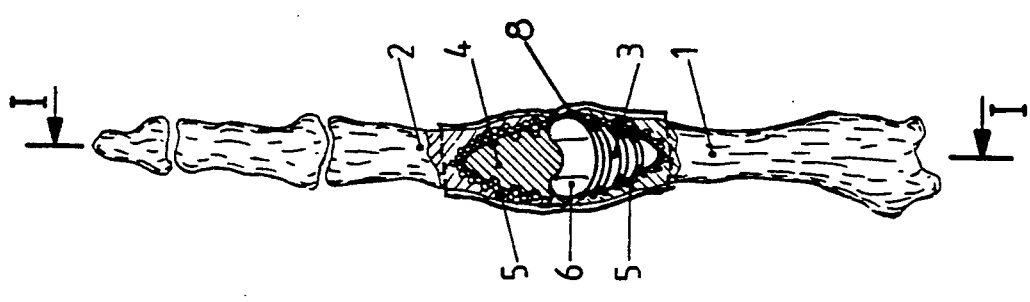

United States Patent
Meuli et al.

[11] Patent Number: 5,092,896
[45] Date of Patent: Mar. 3, 1992

[54] FINGER JOINT PROSTHESIS

[75] Inventors: Hans-Christoph Meuli, Bern; Otto Frey, Winterthur, both of Switzerland

[73] Assignee: Protek AG, Berne, Switzerland

[21] Appl. No.: 587,246

[22] Filed: Sep. 24, 1990

[30] Foreign Application Priority Data

Sep. 28, 1989 [CH] Switzerland .................. 3525/89

[51] Int. Cl.⁵ .................. A61F 2/42; A61F 2/28; A61F 2/30
[52] U.S. Cl. .................. 623/21; 623/16; 623/18
[58] Field of Search .................. 623/21, 16, 18, 20

[56] References Cited

U.S. PATENT DOCUMENTS

| | | | |
|---|---|---|---|
| 3,879,767 | 4/1975 | Stubstad | 623/21 |
| 4,097,935 | 7/1978 | Jarcho | 623/16 |
| 4,231,121 | 11/1980 | Lewis | 623/21 |
| 4,685,919 | 8/1987 | Niwa et al. | 623/21 |

FOREIGN PATENT DOCUMENTS

| | | | |
|---|---|---|---|
| 0176711 | 4/1986 | European Pat. Off. | 623/16 |
| 2605878 | 5/1988 | France | 623/21 |

*Primary Examiner*—Ronald Frinks
*Attorney, Agent, or Firm*—Kenyon & Kenyon

[57] ABSTRACT

A finger joint prosthesis is provided with consists of two pegs of sintered hydroxylapatite for anchoring in adjacent finger bones and which is provided with an intermediate slide layer of polyurethane between the pegs to permit relative movement therebetween. The pegs together with the intermediate layer which may be anchored on one of the pegs form concave and convex bearing areas mating with each other to allow a guided motion in the bend-stretch plane.

12 Claims, 1 Drawing Sheet

FINGER JOINT PROSTHESIS

This invention relates to a finger joint prosthesis.

Heretofore, various types of finger joint prostheses have been known, such as described in Swiss Patent 542,624 and in German Patents 2338136 and 2338137. In each case, the described finger joint prosthesis has been constructed in the manner of a hinge construction wherein a mechanical primary anchorage has been obtained by spreading a peg or sleeve into a shortened and pre-drilled bone member.

U.S. Pat. Nos. 4,685,919 and 4,231,121 as well as French Patent 2605878 also describe other types of two-part prostheses for implantation in a finger to provide a finger joint.

Finger joint prostheses are relatively rare since finger surgery with material from the same body has reached a high level. Generally, finger joint prostheses are suggested in cases where there has been a joint alteration, for example, because of rheumatoid arthritis and arthrosis. However, in such cases, there is usually a very high degree of destruction present of the ligaments and of the joint capsule environment as well. Consequently, an artificial finger joint has a primary function in maintaining position while at the same time guaranteeing adequate primary lateral stability.

Accordingly, it is an object of the invention to provide a finger joint prosthesis which can be implanted in a secure manner while at the same time providing a reliable articulated joint.

It is another object of the invention to provide a finger joint prosthesis which can be used to restore function to a finger joint part.

It is another object of the invention to provide a relatively simple finger joint prosthesis which can be readily implanted.

Briefly, the invention provides a finger joint prosthesis comprised of two pegs of sintered hydroxylapatite for anchoring in two adjacent finger bones and an intermediate slide layer between and separating the pegs in order to permit relative movement between the pegs and being of a material to impede build-up of bone.

The pegs of the finger joint prosthesis may each be tapered and each is provided with a plurality of undercuts and grooves in an outer surface for primary ingrowth of bone.

One advantage of the pegs is that each is made of a material which promotes the formation of bone without itself decomposing too rapidly. As a result, the formation of bone is promoted and at the same time, the possibility arises of recovering a partial function of each finger joint particularly in an age group which previously has been excluded as candidates for a finger joint implant. In this respect, the formation of bone is assisted by a constant not too great a loading.

The intermediate layer may be anchored in one of the pegs while having mating bearing surfaces with the other peg. For example, one of the bearing surfaces may be concave while the other bearing surface is convex. In addition, the slide layer is made of polyurethane or other biocompatible plastics.

In order to provide sufficient lateral stability to the finger after implantation until bone has grown in, the prosthesis may be provided with an elastic hose of resorbable material which surrounds the joint including pegs and intermediate layer. For example, the hose may be made of gelatin or polylactate.

Figure 1:
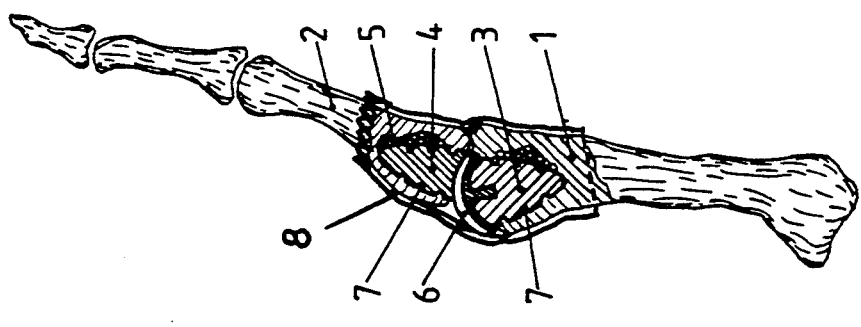

These and other objects and advantages of the invention will become more apparent from the following detailed description taken in conjunction with the accompanying drawings wherein:

FIG. 1 illustrates a view taken on line I—I of FIG. 2 of a finger joint prosthesis implanted in a finger in accordance with the invention; and FIG. 2 illustrates a plan view of the bones of a finger with a prosthesis inserted in accordance with the invention.

Referring to FIGS. 1 and 2, the finger joint prosthesis is to be implanted between two bones 1, 2 of a finger. As illustrated, the prosthesis includes a pair of pegs 3, 4, each of which is implanted in a respective finger bone 1, 2.

Each peg 3, 4 is tapered and consists of a sintered structure of hydroxylapatite. The pegs 3, 4 are separated from one another by an intermediate layer 6 of polyurethane or other biocompatible plastic which is capable of sliding and which impedes the build-up of bone. The intermediate layer 6 is itself anchored to the proximal peg 3 and has a bearing surface which mates with and slides on a bearing surface on the distal peg 4. As illustrated in FIG. 2, the distal peg 4 has a convex surface extending as a rib along the surface while the intermediate layer 6 has a groove of concave shape disposed between two shoulders. As illustrated in FIG. 1, the mating surfaces of this distal peg 4 and the intermediate layer 6 are curvilinear to allow a guided motion in the bend-stretch plane.

In order to enhance anchorage, each peg 3, 4 is provided with undercuts 7 and grooves which secure the peg in place after the ingrowth of bone tissue. Upon introduction, each peg 3, 4 is wedged by granulate 5 of hydroxylapatite and all of the cavities between the pegs 3, 4 and the associated ends of the bones 1, 2 are plugged with granulate 5 of hydroxylapatite. In this way, the granulate with a high surface factor leads relatively rapidly to the formation of bone.

It is to be noted that the dimensions of the implanted finger joint prosthesis are kept larger than the original joint.

In order to provide the finger joint with sufficient lateral stability until the growth of the capsular ligament, an elastic hose 8 or stocking of resorbable material, for example as gelatin or polylactate may be pulled over the finger joint and the prosthesis.

When implanted, the motion of the joint is guided in one plane by the bearing areas of the intermediate layer 6 and the distal peg 4 so long as retaining forces hold the joint together.

The elastic hose 8 which is used for wrapping of the finger joint together with the inserted prosthesis is such that, on the one hand the hose exhibits enough stiffness to achieve adequate primary lateral stability of the finger and, on the other hand, is resorbable over time.

The invention thus provides a finger joint prosthesis which can be readily implanted into a finger joint in which there has been a high degree of destruction. Further, the prosthesis provides for a rapid ingrowth of bone tissue while at the same time providing guided motion in the bend-stretch plane.

The invention further provides a finger joint prosthesis which is able to provide a position maintaining function while at the same time providing for adequate primary lateral stability.

What is claimed is:

1. A finger joint prosthesis comprising a first peg of sintered hydroxylapatite for anchoring in one finger bone;

a second peg of sintered hydroxylapatite for anchoring in a second finger bone;

an intermediate slide layer between and separating said pegs to permit relative movement between said pegs and being of a material to impede build-up of bone; and an elastic hose of resorbable material surrounding said pegs and said intermediate layer.

2. A finger joint prosthesis as set forth in claim 1 wherein each peg is tapered and has a plurality of undercuts in an outer surface for ingrowth of bone therein.

3. A finger joint prosthesis as set forth in claim 1 wherein said intermediate layer and one of said pegs have mating bearing surfaces facing each other with one of said surfaces being concave and the other of said surfaces being convex.

4. A finger joint prosthesis as set forth in claim 1 wherein said intermediate layer is anchored in one of said pegs.

5. A finger joint prosthesis as set forth in claim 4 wherein said layer and the other of said pegs have mating bearing surfaces facing each other with one of said surfaces being concave and the other of said surfaces being convex.

6. A finger joint prosthesis as set forth in claim 1 wherein said layer is made of polyurethane.

7. A finger joint prosthesis as set forth in claim 1 wherein said hose is made of one of gelatin and polylactate.

8. A finger joint prosthesis comprising a first tapered peg of sintered hydroxylapatite for anchoring in one finger bone;

a second tapered peg of sintered hydroxylapatite for anchoring in a second finger bone;

an intermediate layer anchored on one of said pegs for sliding of the other of said pegs thereon and being of a material to impede bone build-up; and an elastic hose of resorbable material surrounding said pegs and said intermediate layer.

9. A finger joint prosthesis as set forth in claim 8 wherein each peg has a plurality of undercuts in an outer surface.

10. A finger joint prosthesis as set forth in claim 8 wherein said layer is made of polyurethane or other biocompatible plastics.

11. A finger joint prosthesis as set forth in claim 8 wherein said layer and said other peg have mating bearing surfaces facing each other with one of said surfaces being concave and the other of said surfaces being convex.

12. A finger joint prosthesis as set forth in claim 8 wherein said hose is made of one of gelatin and polylactate.

* * * * *